DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED JULY 25, 1972

900. O.G. 1230

T900,015

PROCESS FOR PREPARING TRIMETHYL-HYDROQUINONE

John G. Thweatt, Rte. 11 37462, and Fred H. Rash, 510 Whispering Way 37663, both of Kingsport, Tenn.

Filed Oct. 1, 1970, Ser. No. 77,377

Int. Cl. C07c *39/08, 69/16*

U.S. Cl. 260—621 R

No Drawing. 9 Pages Specification

Process for preparing trimethylhydroquinone by contacting 2,6,6-trimethylcyclohex-2-ene-1,4-dione with an acylating agent in the presence of an acid catalyst. Trimethylhydroquinone diester is formed first, which may be hydrolyzed by treatment with aqueous acid or base. When the hydrolysis mixture cools, trimethylhydroquinone may be separated therefrom.